United States Patent
Marchitto et al.

(10) Patent No.: US 9,968,552 B2
(45) Date of Patent: May 15, 2018

(54) PHARMACEUTICAL ORAL DOSAGE FORM COMPRISING A NON-STEROIDAL ANTI-INFLAMMATORY DRUG, AND HAVING GOOD PALATABILITY

(75) Inventors: Leonardo Marchitto, Cupra Marittima (IT); Francesca Mariotti, Pesaro (IT); Lorella Ragni, Chiaravalle (IT)

(73) Assignee: AZIENDE CHIMICHE RIUNITE ANGELINI FRANCESCO A.C.R.A.F.S.p.A., Rome (IT)

( * ) Notice: Subject to any disclaimer, the term of this patent is extended or adjusted under 35 U.S.C. 154(b) by 2217 days.

(21) Appl. No.: 10/582,858

(22) PCT Filed: Dec. 16, 2004

(86) PCT No.: PCT/EP2004/014465
§ 371 (c)(1),
(2), (4) Date: Aug. 14, 2008

(87) PCT Pub. No.: WO2005/058276
PCT Pub. Date: Jun. 30, 2005

(65) Prior Publication Data
US 2008/0292606 A1 Nov. 27, 2008

(30) Foreign Application Priority Data
Dec. 19, 2003 (IT) ............... MI2003A2523

(51) Int. Cl.
*A61K 9/00* (2006.01)
*A61K 47/18* (2017.01)
*A61K 47/22* (2006.01)

(52) U.S. Cl.
CPC ............ *A61K 9/006* (2013.01); *A61K 9/0095* (2013.01); *A61K 47/183* (2013.01); *A61K 47/22* (2013.01)

(58) Field of Classification Search
CPC ..................................... A61K 9/006
See application file for complete search history.

(56) References Cited

U.S. PATENT DOCUMENTS

| 4,518,608 A | 5/1985 | Kahan |
| 5,183,829 A | 2/1993 | Caldwell |
| 5,296,236 A * | 3/1994 | Santus et al. ............. 424/484 |
| 5,653,993 A * | 8/1997 | Ghanta ............ A61K 9/0056 424/440 |
| 2002/0028238 A1 | 3/2002 | Karim et al. |
| 2003/0003152 A1* | 1/2003 | Ream et al. ............. 424/479 |

FOREIGN PATENT DOCUMENTS

| EP | 0 259 990 | 3/1988 |
| EP | 1 974 751 | 10/2008 |
| WO | WO 9718245 A1 * | 5/1997 |
| WO | 03/094905 | 11/2003 |

OTHER PUBLICATIONS

Redenti et al, "Cyclodextrin complexes of salts of acidic drugs. Thermodynamic properties, structural features, and pharmaceutical applications," Journal of Pharmaceutical Sciences, vol. 90, Issue 8, pp. 979-986 (2001).*
Barbanoj, Manel J. et al., "Pharmacokinetics of Dexketoprofen Trometamol in Healthy Volunteers After Single and Repeated Oral Doses", Journal of Clinical Pharmacology, vol. 38, No. 12, pp. 335-405, 1998.
Breslin, Paul A.S. et al., "Ibuprofen as a Chemesthetic Stimulus: Evidence of a Novel Mechanism of Throat Irritation", Chem. Senses, vol. 26, pp. 55-65, 2001.
Breslin, et al., "Ibuprofen as a Chemesthetic Stimulus: Evidence of a Novel Mechanism of Throat Irritation", CHEM. Senses, vol. 26, pp. 55-65, 2001.

* cited by examiner

Primary Examiner — Dennis J Parad
(74) Attorney, Agent, or Firm — Oblon, McClelland, Maier & Neustadt, L.L.P.

(57) ABSTRACT

Oral pharmaceutical dosage form comprising tromethamine and a NSAID selected from the group comprising ibuprofen, naproxen and flurbiprofen, characterized in that it also comprises a compound selected from the group comprising glycine, vitamin B6 and mixtures thereof.

10 Claims, No Drawings

PHARMACEUTICAL ORAL DOSAGE FORM COMPRISING A NON-STEROIDAL ANTI-INFLAMMATORY DRUG, AND HAVING GOOD PALATABILITY

The present invention relates to a pharmaceutical oral dosage form comprising a non-steroidal anti-inflammatory drug (NSAID), and having good palatability.

More particularly, the present invention relates to an oral dosage form comprising
- a NSAID selected from the group comprising ibuprofen, naproxen and flurbiprofen,
- tromethamine, and
- a compound selected from the group comprising glycine, vitamin B6, and mixtures thereof.

In the present description and in the claims, both the terms "NSAID" and "non-steroidal anti-inflammatory drug" mean ibuprofen, naproxen and flurbiprofen as racemate mixtures or as pure or enriched enantiomer forms as well as pharmaceutically acceptable salts.

It is known that a number of non-steroidal anti-inflammatory drugs (NSAIDs), such as ibuprofen, have a "chemesthetic effect" (irritant effect) on the oral cavity, throat and pharynx (Breslin et al. "Ibuprofen as a chemesthetic stimulus: evidence of a novel mechanism of throat irritation", Chem. Sens. 26:55-65, 2001).

This makes irritant and unpleasant the pharmaceutical dosage forms for oral use containing ibuprofen, naproxen, flurbiprofen or enantiomers and/or salts thereof, when such pharmaceutical forms are, for example, partially swallowable or chewable tablets, orosoluble tablets, granulates and powders to be suspended or dissolved before administration, mouthwashes, sprays, cough drops, lozenges, syrups, drops, oral gels and the like.

In the present description and in the claims, the term "oral use" embraces both systemic oral administration and topical oral administration, and the term "oral form" means a pharmaceutical dosage form for oral use.

Many investigations have been carried out so far to improve the patient tolerability of oral forms based on ibuprofen, naproxen and fluriprofen.

However, the ingredients that have been found to be capable of reducing the irritant stimulus on the on the oral cavity, throat and pharynx have also been found to give to the oral forms taste properties, such as bitterness, saltiness and lye-taste, that resulted to be unacceptable.

Therefore, there is still a great need for ingredients capable not only of eliminating the throat-irritant stimulus, but also of giving an acceptable taste, i.e. good palatability, to the oral forms based on ibuprofen, naproxen or flurbiprofen.

Surprisingly it has now been found that this goal is achieved when a compound selected from the group comprising glycine, vitamin B6 and mixtures thereof, is added to an oral form comprising tromethamine and a NSAID selected from the group comprising ibuprofen, naproxen and flurbiprofen.

Therefore, in a first aspect the present invention relates to an oral form comprising tromethamine and a NSAID selected from the group comprising ibuprofen, naproxen and flurbiprofen, characterized in that it also comprises a compound selected from the group comprising glycine, vitamin B6 and mixtures thereof.

Preferably the amount of tromethamine ranges from 0.2 to 50 parts by weight per 1 part by weight of NSAID. More preferably the amount of tromethamine ranges from 1.4 to 2.5 parts by weight and, even more preferably, from 1.4 to 2.2 parts by weight per 1 part by weight of NSAID.

Preferably, the amount of glycine ranges from 0.01 to 20 parts by weight per 1 part by weight of NSAID. More preferably, the amount of glycine ranges from 0.0125 to 10 parts by weight per 1 part by weight of NSAID.

In turn, also the amount of vitamin B6 ranges from 0.01 to 20 parts and, more preferably, from 0.0125 to 10 parts by weight per 1 part by weight of NSAID.

Tolerability and palatability of the oral form of the present invention have been investigated in vivo in man by means of the comparison tests described hereinbelow.

The following examples are intended to further illustrate the invention, without, however, limiting it in any way.

COMPARISON EXAMPLE 1

| Solution A | |
|---|---|
| Ingredients | Amount (g) |
| Ibuprofen sodium | 0.400 |
| Demineralized water | qs 100 ml | pH 7.0-7.5

COMPARISON EXAMPLE 2

| Solution B | |
|---|---|
| Ingredients | Amount (g) |
| Flurbiprofen sodium | 0.250 |
| Demineralized water | qs 100 ml | pH 7.0-7.5

COMPARISON EXAMPLE 3

| Solution C | |
|---|---|
| Ingredients | Amount (g) |
| Naproxen sodium | 0.220 |
| Demineralized water | qs 100 ml |

COMPARISON EXAMPLE 4

| Solution D | |
|---|---|
| Ingredients | Amount (g) |
| Ibuprofen sodium | 0.400 |
| Tromethamine | 0.600 |
| Demineralized water | qs 100 ml |

COMPARISON EXAMPLE 5

| Solution E | |
|---|---|
| Ingredients | Amount (g) |
| Flurbiprofen sodium | 0.250 |
| Tromethamine | 0.500 |
| Demineralized water | qs 100 ml |

COMPARISON EXAMPLE 6

| Solution F | |
|---|---|
| Ingredients | Amount (g) |
| Naproxen sodium | 0.220 |
| Tromethamine | 0.400 |
| Demineralized water | qs 100 ml |

INVENTION EXAMPLE 1

| Solution G | |
|---|---|
| Ingredients | Amount (g) |
| Ibuprofen | 0.400 |
| Tromethamine | 0.600 |
| Glycin | 0.200 |
| Demineralized water | qs 100 ml |

INVENTION EXAMPLE 2

| Solution H | |
|---|---|
| Ingredients | Amount (g) |
| Flurbiprofen | 0.250 |
| Tromethamine | 0.500 |
| Glycin | 0.010 |
| Demineralized water | qs 100 ml |

INVENTION EXAMPLE 3

| Solution I | |
|---|---|
| Ingredients | Amount (g) |
| Naproxen sodium | 0.220 |
| Tromethamine | 0.400 |
| Glycin | 0.145 |
| Demineralized water | qs 100 ml |

INVENTION EXAMPLE 4

| Water-soluble Granulate (L) | |
|---|---|
| Ingredients | Amount (g) |
| Ibuprofen 80 BP | 0.400 |
| Sodium saccharine | 0.030 |
| Tromethamine | 0.600 |
| Lemon flavouring Givaudan 96833-51 | 0.100 |
| Acesulfame K | 0.030 |
| Vitamin B6 | 0.150 |
| Sugar for tabletting | 3.000 |
| Sucrose monopalmitate | 0.020 |

INVENTION EXAMPLE 5

| Oral spray (M) | |
|---|---|
| Ingredients | Amount (g) |
| Flurbiprofen | 0.250 |
| Glycerol FU IX | 10.000 |
| 95° ethyl alcohol | 10.000 |
| Sorbitol 70 | 7.000 |
| Sodium saccharine | 0.150 |
| Tromethamine | 0.500 |
| Sodium benzoate | 0.150 |
| Tween 20 | 1.000 |
| Mint cool flavour | 0.195 |
| Blu patent | 0.0006 |
| Glycin | 0.010 |
| Demineralized water | qs 100 ml |

INVENTION EXAMPLE 6

| Water-soluble Granulate (N) | |
|---|---|
| Ingredients | Amount (g) |
| Naproxen sodium | 0.220 |
| Sodium saccharine | 0.032 |
| Peppermint flavouring Givaudan | 0.093 |
| Acesulfame K | 0.030 |
| Maltitol | 1.500 |
| Glycin | 0.145 |
| Sucrose | 1.500 |
| Tromethamine | 0.400 |

PALATABILITY TEST

The panel of individuals for the palatability (taste masking) test of the oral forms under evaluation has been properly selected because the irritation of the oral mucosae by the NSAIDs shows great individual variability. Indeed, whereas for some individuals the irritation may be "slightly noticeable", others define it as "strong" or "very strong" (Breslin et al. "Ibuprofen as a chemesthetic stimulus: evidence of a novel mechanism of throat irritation", Chem. Sens. 26:55-65, 2001).

There were therefore selected individuals who proved to be clearly sensitive to the irritant action of the NSAIDs in the test disclosed hereinafter.

Solutions A to C were administered to 40 individuals between 20 and 40 years old, and indications were given for correctly defining the perceived irritant stimulus, as follows:

| Stimulus | Description |
| --- | --- |
| Burning | Sensation generated by abrasion of the skin or by exposure to high temperature, or to the irritant action of alcohol |
| Stinging | Brief sensation produced as from an insect bite or from thorns |
| Prickling | Sensation similar to that caused by the action of small penetrating needles |
| Numbness | Diffuse sensation similar to the start of action of an anaesthetic (not an absence of sensation) |

In addition, the 40 individuals were given instructions regarding the following operating procedures:
  how to define the sensation perceived according to the terminology defined in the preceding table,
  how to perform the operations of rinsing, swallowing and spraying of the preparations and also how to recognize the background sensation caused the preparations free of active principle.

Each of the 40 individuals was also requested to follow the standard procedure hereinbelow when taking the preparations:
  sip 10 ml of demineralized water, hold it in the mouth for 10 seconds and then swallow it,
  sip 10 ml of Solution, hold it in the mouth for 10 seconds and then swallow it.

Next, the 40 individuals were asked to evaluate the intensity of the irritation in the oral cavity and the perceived taste at time 0, at 30 seconds, 1 minute and 5 minutes after the administration, and 3 points were assigned to those who defined the sensation as "strong", 2 points to those who define defined the sensation as "moderate", 1 point to those who defined the sensation as "mild" and 0 points to those who defined the preparation as having no sensation.

Only the 18 individuals who received more than 40 points, and who therefore had greater sensitivity of perception of the unpleasant sensations generated by the NSAIDs, were thus selected.

These 18 individuals were requested to evaluate the palatability of the solutions D to F as well as the aqueous solutions of the granulates L and N and the oral spay M.

The procedure followed and the points assigned were as for those described above, except that, in the case of the spray, the patients sprayed in the mouth two puffs of 200 µl and then swallowed the sprayed spray, whereas in the case of the granulate, each patient was administered the content (average weight=4.33 g) of a sachet dissolved in 100 ml of water and stirred for 30 seconds.

In addition, the evaluation times were longer, since the 18 individuals were requested to evaluate the intensity of the irritation in the mouth and the perceived taste at time 0, at 30 seconds, 1 minute, 2 minutes, 3 minutes, 5 minutes, 10 minutes and 15 minutes after the administration.

The sum of the evaluations (0-15 minutes) for, respectively, the burning, the stinging, the prickling and the numbness etc. was calculated for each individual, along with the sum of the evaluations (0-15 minutes) for all the sensations. These parameters were analysed by the Wilcoxon "signed rank" method to compare the solutions and oral forms containing the same active ingredient. The final scores are shown in the following Table.

TABLE

| Composition | Active Ingredient | Score |
| --- | --- | --- |
| Solution A | Ibuprofen | 21 |
| Solution D | " | 16 |

TABLE-continued

| Composition | Active Ingredient | Score |
| --- | --- | --- |
| Solution G | " | 11 |
| Granulate L | " | 8 |
| Solution B | Flurbiprofen | 15 |
| Solution E | " | 12 |
| Solution H | " | 9 |
| Oral Spray M | " | 6 |
| Solution C | Naproxen | 20 |
| Solution F | " | 17 |
| Solution I | " | 10 |
| Granulate N | " | 7 |

The evaluation of the compositions containing ibuprofen showed that Solution G and the solution of Granulate L of the invention were less irritant and unpleasant and had a better palatability than the comparison Solutions A and D, not only for each individual sensation considered, but also for the sum of the evaluations obtained for all the sensations.

The evaluation of the compositions containing flurbiprofen showed that Solution H and the Oral Spray M of the invention were less irritant and unpleasant and had a better palatability than the comparison Solutions B and E, not only for each individual sensation considered, but also for the sum of the evaluations obtained for all the sensations.

The evaluation of the compositions containing naproxen showed that Solution I and the solution of Granulate N of the invention were less irritant and unpleasant and had a better palatability than the comparison Solutions C and F, not only for each individual sensation considered, but also for the sum of the evaluations obtained for all the sensations.

The invention claimed is:

1. A pharmaceutical oral dosage form consisting of
  tromethamine;
  a NSAID selected from the group consisting of ibuprofen and flurbiprofen;
  a compound selected from the group consisting of glycine, vitamin B6 and mixtures thereof; and
  at least one additive selected from the group consisting of sodium saccharine, lemon flavoring, acesulfame K, sugar, sucrose monopalmitate, glycerol, ethyl alcohol, sorbitol 70, sodium benzoate, tween 20, mint flavoring, blu patent, demineralized water, peppermint flavoring, maltitol, and sucrose;
  wherein said pharmaceutical oral dosage form contains from 0.2 to 2.5 parts by weight of tromethamine per one part by weight of NSAID.

2. A pharmaceutical oral dosage form according to claim 1, containing from 1.4 to 2.5 parts by weight of tromethamine per one part by weight of NSAID.

3. A pharmaceutical oral dosage form according to claim 1, containing from 1.4 to 2.2 parts by weight of tromethamine per one part by weight of NSAID.

4. A pharmaceutical oral dosage form according to claim 1, containing from 0.01 to 20 parts by weight of glycine per one part by weight of NSAID.

5. A pharmaceutical oral dosage form according to claim 4, containing from 0.0125 to 10 parts by weight of glycine per one part by weight of NSAID.

6. A pharmaceutical oral dosage form according to claim 1, containing from 0.01 to 20 parts by weight of vitamin B6 per one part by weight of NSAID.

7. A pharmaceutical oral dosage form according to claim 6, containing from 0.0125 to 10 parts by weight of vitamin B6 per one part by weight of NSAID.

8. A pharmaceutical oral dosage form according to claim 1, in water-soluble granulate form.

9. A pharmaceutical oral dosage form according to claim 1, in spray form.

10. A pharmaceutical oral dosage form according to claim 1, wherein said additive is at least one additive selected from the group consisting of sodium saccharine, lemon flavoring, acesulfame K, sugar, and sucrose monopalmitate.

* * * * *